United States Patent
Sheldon et al.

(10) Patent No.: US 9,750,943 B2
(45) Date of Patent: Sep. 5, 2017

(54) MONITORING OF PACING CAPTURE USING ACCELERATION

(71) Applicant: Medtronic, Inc., Minneapolis, MN (US)

(72) Inventors: Todd J Sheldon, North Oaks, MN (US); David M Steinhaus, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/681,223

(22) Filed: Apr. 8, 2015

(65) Prior Publication Data

US 2016/0250480 A1    Sep. 1, 2016

Related U.S. Application Data

(60) Provisional application No. 62/121,234, filed on Feb. 26, 2015.

(51) Int. Cl.
*A61N 1/37* (2006.01)
*A61N 1/365* (2006.01)

(52) U.S. Cl.
CPC ....... *A61N 1/3712* (2013.01); *A61N 1/36542* (2013.01); *A61N 1/36578* (2013.01); *A61N 1/36507* (2013.01)

(58) Field of Classification Search
CPC .......................... A61N 1/3712; A61N 1/36542
See application file for complete search history.

(56) References Cited

U.S. PATENT DOCUMENTS

| | | | |
|---|---|---|---|
| 4,485,813 A | 12/1984 | Anderson | |
| 5,052,388 A | 10/1991 | Sivula | |
| 5,507,782 A | 4/1996 | Kieval | |
| 5,549,652 A | 8/1996 | Mcclure | |
| 5,593,431 A | 1/1997 | Sheldon | |
| 5,628,777 A | 5/1997 | Moberg | |
| 5,683,432 A | 11/1997 | Goedeke | |
| 5,693,075 A | 12/1997 | Plicchi | |
| 5,702,427 A * | 12/1997 | Ecker | A61N 1/36542 607/28 |
| 5,720,769 A | 2/1998 | Van Oort | |
| 5,814,089 A | 9/1998 | Stokes | |
| 6,044,297 A | 3/2000 | Sheldon | |

(Continued)

FOREIGN PATENT DOCUMENTS

WO    2005/089866 A1    9/2005

OTHER PUBLICATIONS (PCT/US2016/019883) PCT Notification of Transmittal of the International Search Report and the Written Opinion of the International Searching Authority, mailed Aug. 31, 2016, 18 pages.

*Primary Examiner* — Eric D. Bertram

(57) ABSTRACT

An implantable medical device includes an activity sensor, a pulse generator, and a control module. The control module is configured to determine an activity metric from the activity sensor signal over an activity metric interval and compare the activity metric to a loss of capture detection threshold. The control module may detect loss of capture in response to the activity metric being less than the loss of capture detection threshold and increase a pacing pulse output in response to detecting the loss of capture.

10 Claims, 8 Drawing Sheets

(56) References Cited

U.S. PATENT DOCUMENTS

| | | |
|---|---|---|
| 6,208,900 B1 | 3/2001 | Ecker et al. |
| 6,650,940 B1 | 11/2003 | Zhu |
| 7,031,772 B2 | 4/2006 | Condie |
| 7,123,963 B2 | 10/2006 | Sawchuk |
| 8,214,036 B2 * | 7/2012 | Casset .................. A61N 1/3712 607/9 |
| 8,215,151 B2 | 7/2012 | Sammoura |
| 8,352,030 B2 | 1/2013 | Denison |
| 8,386,042 B2 | 2/2013 | Yudovsky |
| 8,433,409 B2 | 4/2013 | Johnson |
| 8,532,785 B1 | 9/2013 | Crutchfield |
| 8,541,131 B2 | 9/2013 | Lund |
| 2007/0088400 A1 | 4/2007 | Jacobson |
| 2007/0293904 A1 | 12/2007 | Gelbart |
| 2010/0125309 A1 | 5/2010 | Casset |
| 2012/0172892 A1 | 7/2012 | Grubac |
| 2012/0194341 A1 | 8/2012 | Peichel |
| 2013/0035748 A1 | 2/2013 | Bonner |
| 2015/0217119 A1 | 8/2015 | Nikolski et al. |
| 2016/0144191 A1 | 5/2016 | Sheldon et al. |

* cited by examiner

MONITORING OF PACING CAPTURE USING ACCELERATION

CROSS-REFERENCE TO RELATED APPLICATIONS

This application claims the benefit of U.S. Provisional Application No. 62/121,234, filed on Feb. 26, 2015. The disclosure of the above application is incorporated herein by reference in its entirety.

TECHNICAL FIELD

The disclosure relates to an implantable medical device and associated method for monitoring for cardiac pacing capture using an activity sensor signal.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/ or other sensors. Other IMDs may incorporate electrodes and/or other sensors along or within a housing of the IMD that encloses circuitry and electronic components of the IMD.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers monitor a patient's heart activity and provide therapeutic electrical stimulation to the heart of the patient via electrodes coupled to the pacemaker. The electrical stimulation provided by the IMD may include signals such as pacing pulses to address abnormal cardiac rhythms such as bradycardia, tachycardia and fibrillation.

An IMD may sense signals representative of intrinsic depolarizations of the heart and analyze the sensed signals to identify normal or abnormal rhythms. Upon detection of an abnormal rhythm, the device may deliver an appropriate electrical stimulation signal or signals to restore or maintain a more normal rhythm. For example, an IMD may deliver bradycardia pacing, anti-tachycardia pacing (ATP), or cardioversion or defibrillation shocks to the heart upon detecting an abnormal rhythm. A pacing pulse will capture the heart, i.e., successfully cause a pacing-evoked depolarization of the myocardium, if the pacing pulse energy is equal to or greater than the capture threshold.

In some cases, the IMD senses a signal representative of the metabolic demand of the patient in order to provide cardiac pacing at a rate intended to meet the metabolic demand of the patient. For example, an indication of the patient's physical activity level may be determined from an accelerometer signal in order provide rate responsive pacing to dynamically maintain a heart rate that meets the metabolic demand of the patient.

SUMMARY

In general, the disclosure is directed to techniques for monitoring for cardiac pacing capture based on an accelerometer signal. A pacemaker operating in accordance with the techniques disclosed herein confirms capture based on an activity metric determined from the accelerometer signal. If capture is not verified based on the activity metric, the pacing pulse output may be increased to determine a capture threshold.

In one example, the disclosure provides a method for detecting loss of pacing capture in a patient by an implantable medical device. The method includes delivering pacing pulses to a chamber of a heart of the patient, sensing an activity sensor signal comprising motion signals that may correspond to motion of the heart and/or motion signals due to physical activity of the patient, determining an activity metric from the activity sensor signal over an activity metric interval, comparing the activity metric to a loss of capture detection threshold, detecting loss of capture of the delivered pacing pulses in response to the activity metric being less than the loss of capture detection threshold, and increasing a pacing pulse output in response to detecting the loss of capture.

In another example, the disclosure provides an implantable medical device comprising an activity sensor configured to produce a signal including motion signals that may correspond to motion of the heart and/or motion signals due to physical activity of the patient, a pulse generator configured to generate and deliver pacing pulses to the patient's heart via a pair of electrodes coupled to the implantable medical device, and a control module coupled to the pulse generator and the activity sensor. In some examples, the control module is configured to determine an activity metric from the activity sensor signal over an activity metric interval, compare the activity metric to a loss of capture detection threshold, detect loss of capture of the delivered pacing pulses in response to the activity metric being less than the loss of capture detection threshold, and increase a pacing pulse output in response to detecting the loss of capture.

In another example, the disclosure provides a non-transitory, computer readable storage medium storing a set of instructions that, when executed by a control module of an implantable medical device, cause the device to deliver pacing pulses to a chamber of a patient's heart, sense an activity sensor signal comprising motion signals that may correspond to motion of the heart and/or motion signals due to physical activity of the patient, determine an activity metric from the activity sensor signal over an activity metric interval, compare the activity metric to a loss of capture detection threshold, detect loss of capture of the delivered pacing pulses in response to the activity metric being less than the loss of capture detection threshold, and increase a pacing pulse output in response to detecting the loss of capture.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, an implantable medical device (IMD) system is disclosed herein that includes a pacemaker configured to deliver cardiac pacing and confirm pacing capture based at least in part on an activity metric that is determined (directly measured, computed or derived) from an activity sensor signal that may be embodied as an accelerometer. Cardiac capture is the depolarization of a heart chamber in response to an electrical pacing pulse delivered by the pacemaker. The capture threshold is the minimum pacing pulse output, e.g., the minimum pacing pulse amplitude for a given pacing pulse width or vice versa, that successfully captures the paced heart chamber.

A pacemaker configured to detect loss of capture based on an activity sensor signal as described herein may be implanted wholly in a chamber of a patient's heart in some examples. The pacemaker activity sensor, which may be an accelerometer, is subjected to heart motion so that the activity sensor signal comprises motion signals due to heart motion and motion signals due to patient physical activity. Cardiac pacing pulse output is controlled by the pacemaker based at least in part on activity metrics derived from the activity sensor signal.

Figure 1:
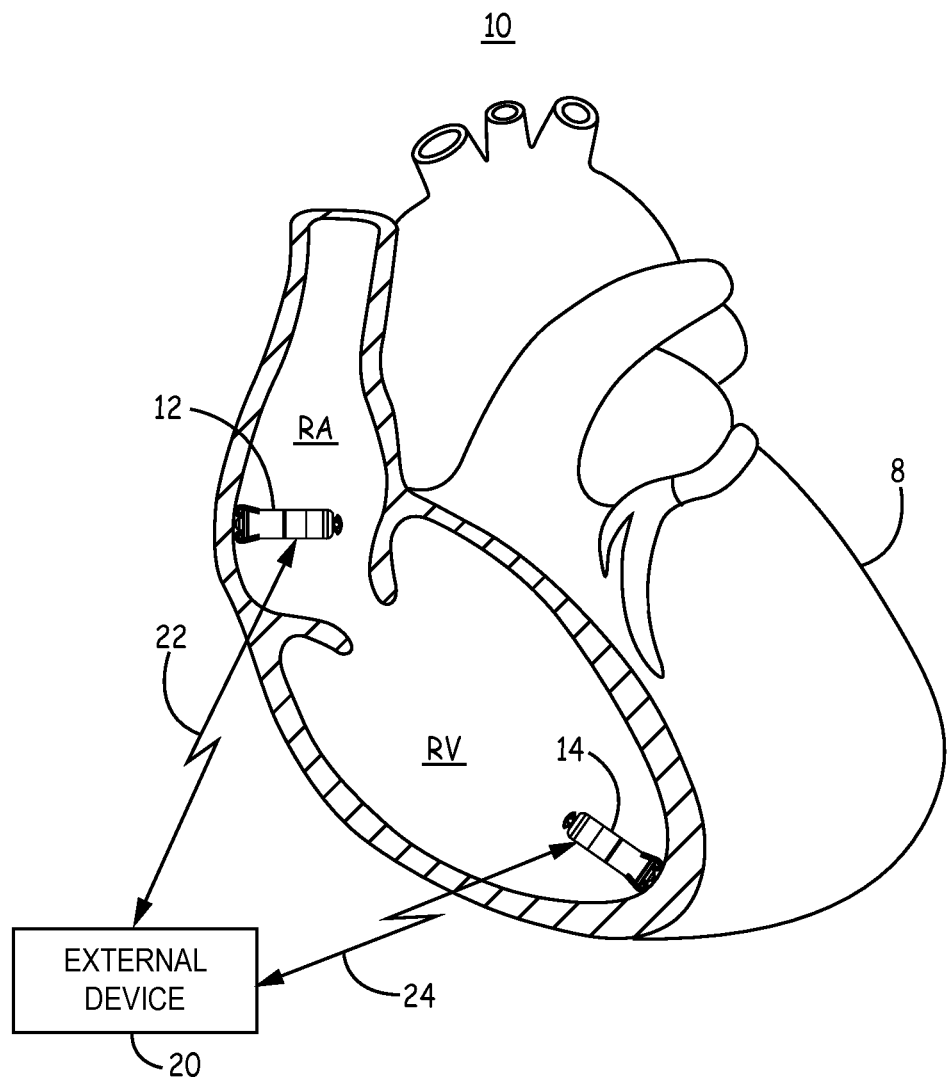
FIG. 1 is a conceptual diagram illustrating an intracardiac pacing system that may be used to sense cardiac electrical signals and provide therapy to a patient's heart.

FIG. 1 is a conceptual diagram illustrating an intracardiac pacing system 10 that may be used to sense cardiac electrical signals and provide therapy to a patient's heart 8. IMD system 10 includes a right ventricular (RV) intracardiac pacemaker 14 and a right atrial (RA) intracardiac pacemaker 12. A cardiac pacing system employing the techniques disclosed herein is not limited to a system including both a RA pacemaker 12 and a RV pacemaker 14. Rather, a cardiac pacing system employing the disclosed techniques may include one or more pacemakers that include an activity sensor that is subjected to the motion of the beating heart 8.

In the example shown, pacemakers 12 and 14 are transcatheter, intracardiac pacemakers adapted for implantation wholly within a heart chamber, e.g., wholly within the RV, wholly within the left ventricle (LV), wholly within the RA or wholly within the left atrium (LA) of heart 8. RA pacemaker 12 is shown positioned along an endocardial wall of the RA, e.g., along the RA lateral wall or RA septum. RV pacemaker 14 is shown positioned along an endocardial wall of the RV, e.g., near the RV apex. The techniques disclosed herein, however, are not limited to the pacemaker locations shown in the example of FIG. 1 and other relative locations within or along the respective heart chambers are possible, including epicardial or pericardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using housing based electrodes and deliver RV pacing pulses.

Pacemakers 12 and 14 are each capable of bidirectional wireless communication with an external device 20. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, such as sensing and therapy delivery control parameters, may be programmed into pacemakers 12 and 14 using external device 20. Aspects of external device 20 may generally correspond to the external programming/monitoring unit disclosed in U.S. Pat. No. 5,507,782 (Kieval, et al.), hereby incorporated herein by reference in its entirety.

External device 20 is configured for bidirectional communication with an implantable telemetry module included in pacemakers 12 and 14. External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat. No. 5,683,432 (Goedeke, et al.), hereby incorporated herein by reference in its entirety. Communication links 22 and 24 may be established between respective RA pacemaker 12 and RV pacemaker 14 and external device 20 using a radio frequency (RF) link in the Medical Implant Communication Service (MICS) band, Medical Data Service (MEDS) band, BLUETOOTH® or Wi-Fi.

External device 20 may be capable of bi-directional communication with pacemakers 12 and 14 over a wide range of distances, e.g., up to approximately 10 meters. In other examples, telemetry communication may require the use of a programming head placed in proximity of RA pacemaker 12 or RV pacemaker 14 to facilitate data transfer. It is contemplated that external device 20 may be in wired or wireless connection to a communication network for transferring and receiving data and to/from a remote database or computer to allow remote management of the patient 12.

Figure 2A:
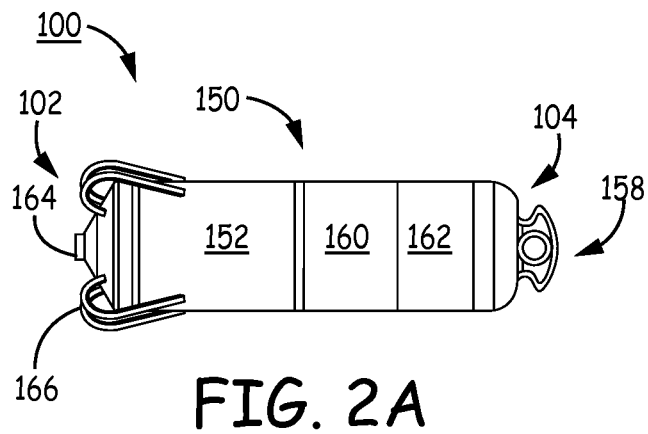
FIG. 2A is a conceptual diagram of an intracardiac pacemaker that may correspond to the RA pacemaker or RV pacemaker shown in FIG. 1.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form a cathode and anode pair for bipolar cardiac pacing and sensing. Electrodes 162 and 164 may be positioned on or as near as possible to respective proximal and distal ends 104 and 102 to increase the inter-electrode spacing between electrodes 162 and 164.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

Figure 2B:
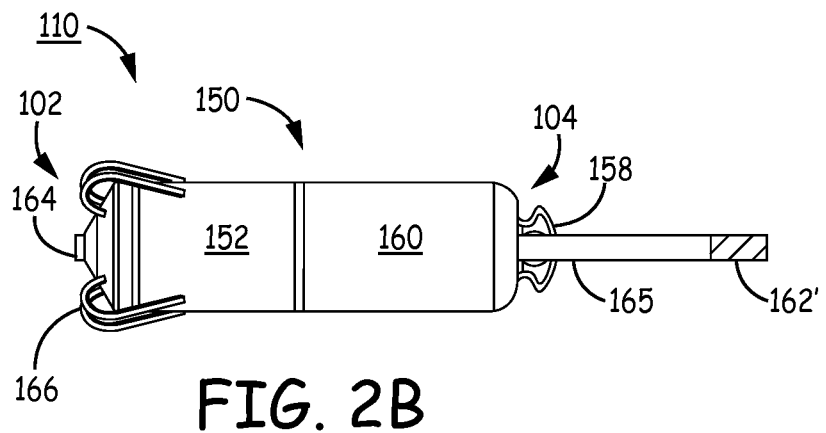
FIG. 2B is a conceptual diagram of an alternative embodiment of an intracardiac pacemaker.

FIG. 2B is a conceptual diagram of an alternative embodiment of an intracardiac pacemaker 110. Pacemaker 110 includes housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an electrically conductive extender 165. As such, instead of carrying a pair of electrodes along the housing 150, which limits the maximum possible inter-electrode spacing, an extender 165 may be electrically coupled to the housing 150 for positioning an electrode 162' at an increased inter-electrode distance from distal tip electrode 164, in which case all or a portion of housing 150 may be insulated.

Figure 2C:
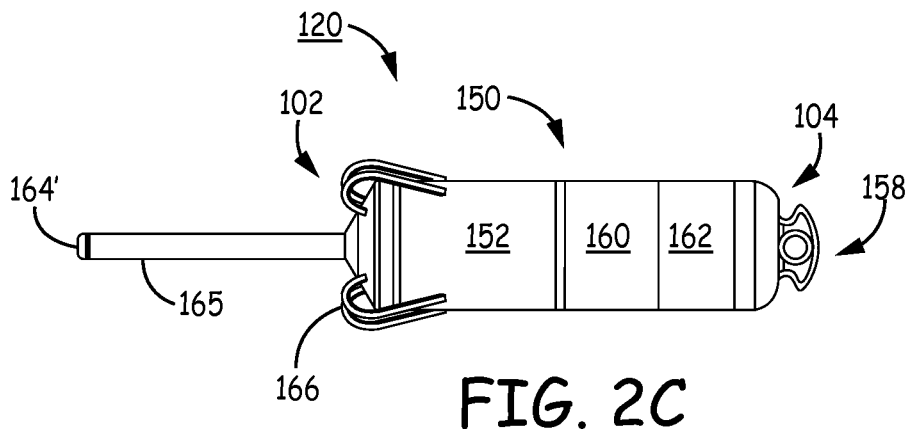
FIG. 2C is a conceptual diagram of another alternative embodiment of an intracardiac pacemaker.

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 shown in FIGS. 2B and 2C is an insulated electrical conductor that electrically couples electrode 162' (FIG. 2B) or electrode 164' (FIG. 2C) to pacemaker circuitry via an electrical feedthrough crossing housing 150. Pacemaker 120 having an insulated, electrically conductive extender 165 for increasing the inter-electrode spacing may correspond generally to the implantable device and flexible conductor disclosed in commonly-assigned, pre-grant U.S. Publication No. 2013/0035748 (Bonner, et al.), hereby incorporated herein by reference in its entirety.

In the examples shown in FIGS. 2A, 2B and 2C, an accelerometer for producing a signal correlated to patient activity may be enclosed in control electronics assembly 152. In other examples, an accelerometer may be located along extender 165 or any other portion of housing 150. The accelerometer may be embodied as a piezoelectric or MEMS accelerometer in some examples.

Figure 3:
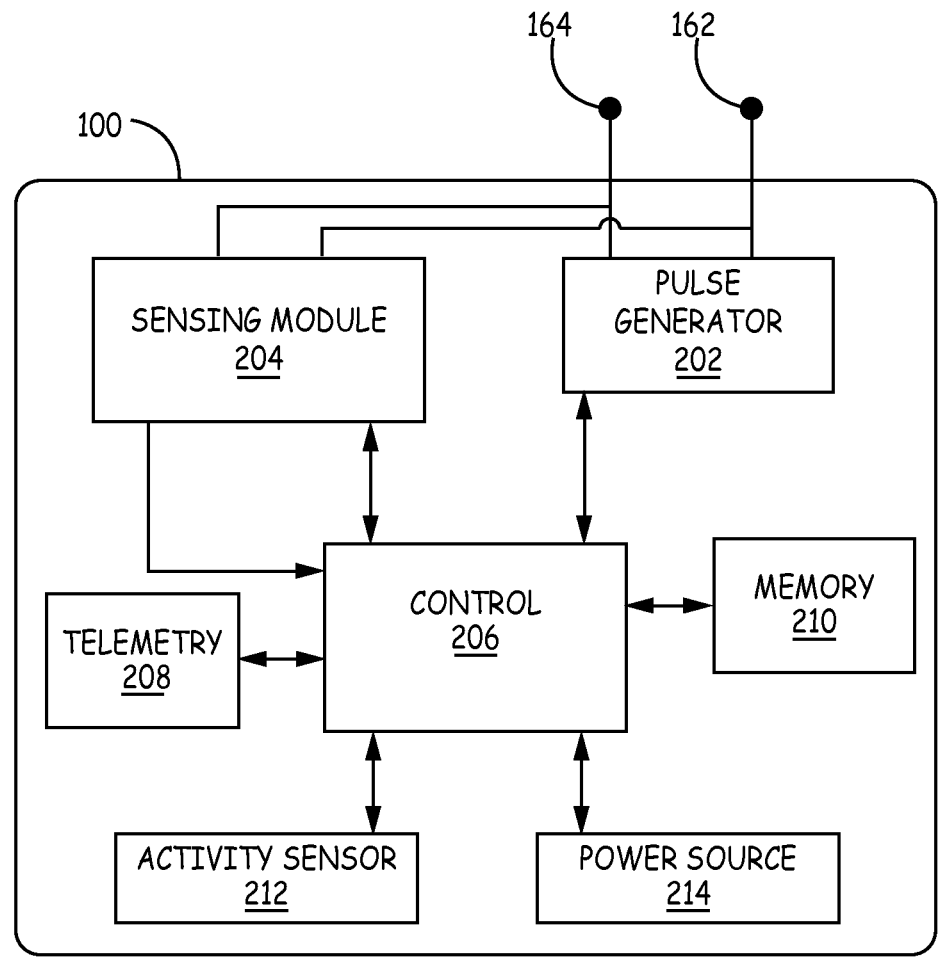
FIG. 3 is a functional block diagram of an example configuration of the pacemaker shown in FIGS. 2A-2C.

FIG. 3 is a functional block diagram of an example configuration of pacemaker 100 shown in FIG. 2A (or pacemaker 110 or pacemaker 120 of FIGS. 2B and 2C, respectively). Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 may include similar modules as represented by the pacemaker 100 shown in FIG. 3; however it is understood that the modules are configured differently as needed to perform the functionality of the separate RA and RV pacemakers 12 and 14.

For example, when pacemaker 100 is configured to operate as RV pacemaker 14, control module 206 is configured to set various ventricular pacing escape intervals used to control delivery of ventricular pacing pulses. When pacemaker 100 is embodied as RA pacemaker 12, control module 206 is configured to set atrial pacing escape intervals to control delivery of RA pacing pulses.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in memory 210 and relying on input from sensing module 204.

The particular form of software, hardware and/or firmware employed to implement the functionality disclosed herein will be determined primarily by the particular system architecture employed in the device and by the particular detection and therapy delivery methodologies employed by the device. Providing software, hardware, and/or firmware to accomplish the described functionality in the context of any modern IMD, given the disclosure herein, is within the abilities of one of skill in the art.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, as controlled by a pace timing and control module included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control module included in control module 206 may include an escape interval timer or counter that is set to a pacing escape interval used for controlling the timing of pacing pulses relative to a paced or sensed event. Upon expiration of a pacing escape interval, a pacing pulse is delivered. If a cardiac event is sensed by sensing module 204 during the pacing escape interval, the scheduled pacing pulse may be inhibited, and the pacing escape interval may be reset to a new time interval.

The control module 206 may set a pulse amplitude and/or pulse width of pacing pulses delivered by pulse generator 202 according to a capture threshold determined during a capture threshold search. Control module 206 may execute a capture threshold search by controlling pulse generator 202 to deliver pacing pulses at decreasing pacing output, for example decreasing pacing pulse amplitude for a given pulse width, until an electrical evoked response is not sensed from the EGM signal by sensing module 204. The lowest pacing pulse output that causes an electrical evoked response is determined as the capture threshold. It is recognized that a capture threshold search may be performed using other signals for detecting a pacing evoked response, and the pacing output may be varied in an increasing, random or other order.

Sensing module 204 receives cardiac EGM signals developed across electrodes 162 and 164. An intrinsic cardiac event may be sensed by sensing module 204 when the EGM signal crosses a sensing threshold, which may be an auto-adjusting sensing threshold. In response to a sensing threshold crossing, sensing module 204 passes a sensed event signal to control module 206 for use in controlling the timing of pacing pulses. Sensing module 204 may be configured to sense a pacing evoked response from the cardiac EGM signal and pass an evoked response detection signal and/or pass a multi-bit digital signal to control module 206 for detection of a pacing evoked response from the EGM signal. Electrical evoked response detection may be used by control module 206 for confirming electrical capture of the heart following a pacing pulse, verifying LOC detected based on an activity sensor signal, and/or for use in determining the capture threshold during a capture threshold search.

Pacemaker 100 may further include one or more other physiological sensors for monitoring the patient, such as a pressure sensor, an acoustical sensor, an oxygen sensor, or any other implantable physiological sensor. In some cases, another signal may be used to verify LOC and/or detect evoked responses during a capture threshold search.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202. For example, memory 210 may store relationships used in determining a sensor-indicated pacing rate based on a signal from activity sensor 212 and store LOC detection control parameters used by control module 206 for detecting LOC based on the activity sensor signal.

Activity sensor 212 may be embodied as a piezoelectric accelerometer, MEMS accelerometer, or other sensor that produces a signal correlated to patient body motion, including heart motion and motion due to physical activity of the patient. Activity sensor 212 may correspond to the accelerometer disclosed in commonly-assigned U.S. Pat. No. 8,352,030 (Denison, et al.) or U.S. Pat. No. 8,386,042 (Yudovsky, et al.), both of which patents are incorporated herein by reference in their entirety. A pacemaker arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety.

Activity sensor 212 may include a single axis accelerometer or a multi-axis accelerometer, e.g. three orthogonal axes, having sensitivity to motion in three dimensions. A multi-dimensional accelerometer is generally disclosed in in U.S. Pat. No. 5,593,431 (Sheldon), hereby incorporated herein by reference in its entirety. The use of an accelerometer in an intracardiac device for obtaining a patient activity signal is generally disclosed in U.S. patent application Ser. No. 14/174,514 filed on Feb. 6, 2014 (Nikolski, et al.), incorporated herein by reference in its entirety. The use of a patient activity signal for providing rate-responsive pacing is generally disclosed in U.S. Pat. No. 7,031,772 (Condie, et al.), incorporated herein by reference in its entirety.

Control module 206 may be configured to use a signal from activity sensor 212 for determining a sensor-indicated rate (SIR) used to control the rate of pacing pulse delivery to meet the patient's metabolic demand. For example, an escape interval timer included in control module 206 may be set to a pacing escape interval corresponding to a SIR, and the pacing escape interval may be adjusted as the SIR changes in response to the activity sensor signal. Control module 206 receives an activity signal from activity sensor 212 and determines an activity metric from the signal at desired intervals for use in determining the SIR. The SIR may vary between a programmed or predetermined lower rate (LR) during periods of rest and a programmed maximum upper pacing rate during periods of maximum exertion. The SIR may be controlled according to a SIR transfer function, which may include different rates of change of the SIR over different ranges of the activity metric.

In some examples, the activity metric is determined as an activity count. In these instances, control module 206 may include a counter to track the activity count as the number of times the signal from activity sensor 212 crosses an activity signal threshold during an activity count interval, for example a 2-second interval. The count at the end of each activity count interval is correlated to patient body motion during the activity count interval and is therefore correlated to patient metabolic demand. The threshold applied to the activity sensor signal, which when crossed by the activity sensor signal causes the activity count to be increased, may be a default or programmable threshold or may be an automatically adjusted threshold. Methods for obtaining an activity count over an n-second interval and for adjusting the activity sensor signal threshold used for obtaining the activity count are generally disclosed in commonly-assigned U.S. Pat. No. 5,720,769 (van Oort), incorporated herein by reference in its entirety. In other examples, an activity metric may be obtained from the activity sensor signal by integrating or summing activity signal sample points of the rectified activity sensor signal over an activity count interval, e.g., a two-second interval though longer or shorter intervals of time may be used for determining an activity metric.

Control module 206 is configured to verify capture of a pacing pulse delivered by pulse generator 202 based on a signal received from activity sensor 202. As described below, an activity metric determined from the activity sensor 202 may be compared to loss of capture criteria to detect lost capture. In some cases, the activity metric used to detect loss of capture is the same activity metric that is computed for the same time interval that is used to determine the SIR for controlling pacing rate. When pacemaker 100 is located within or along a heart chamber, the activity sensor signal will include heart motion signals. When loss of capture occurs due to pacing pulse output being below the capture threshold, asystole may occur. The contribution of the heart motion to the activity sensor signal will decrease if asystole occurs, which may decrease the activity metric derived from the activity sensor signal. Control module 206 may be configured to detect loss of capture based on a decrease of the activity metric derived from the activity sensor signal below a loss of capture detection threshold. Control module 206 may respond to detecting loss of capture detection based on an activity metric to re-establish pacing pulse delivery above the heart chamber capture threshold.

Power source 214 provides power to each of the other modules and components of pacemaker 100 as required. Control module 206 may execute power control operations to control the timing for powering on or off various components or modules to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data from external device 20 via a radio frequency (RF) communication link as described above. Pacemaker 100 may receive pacing and sensing control parameter values and loss of capture detection control parameters via programming commands received by telemetry module 208 from external device 20. Various control parameter values may be stored in memory 210 for access by control module 206 for performing sensing, pacing and capture management functions.

Figure 4:
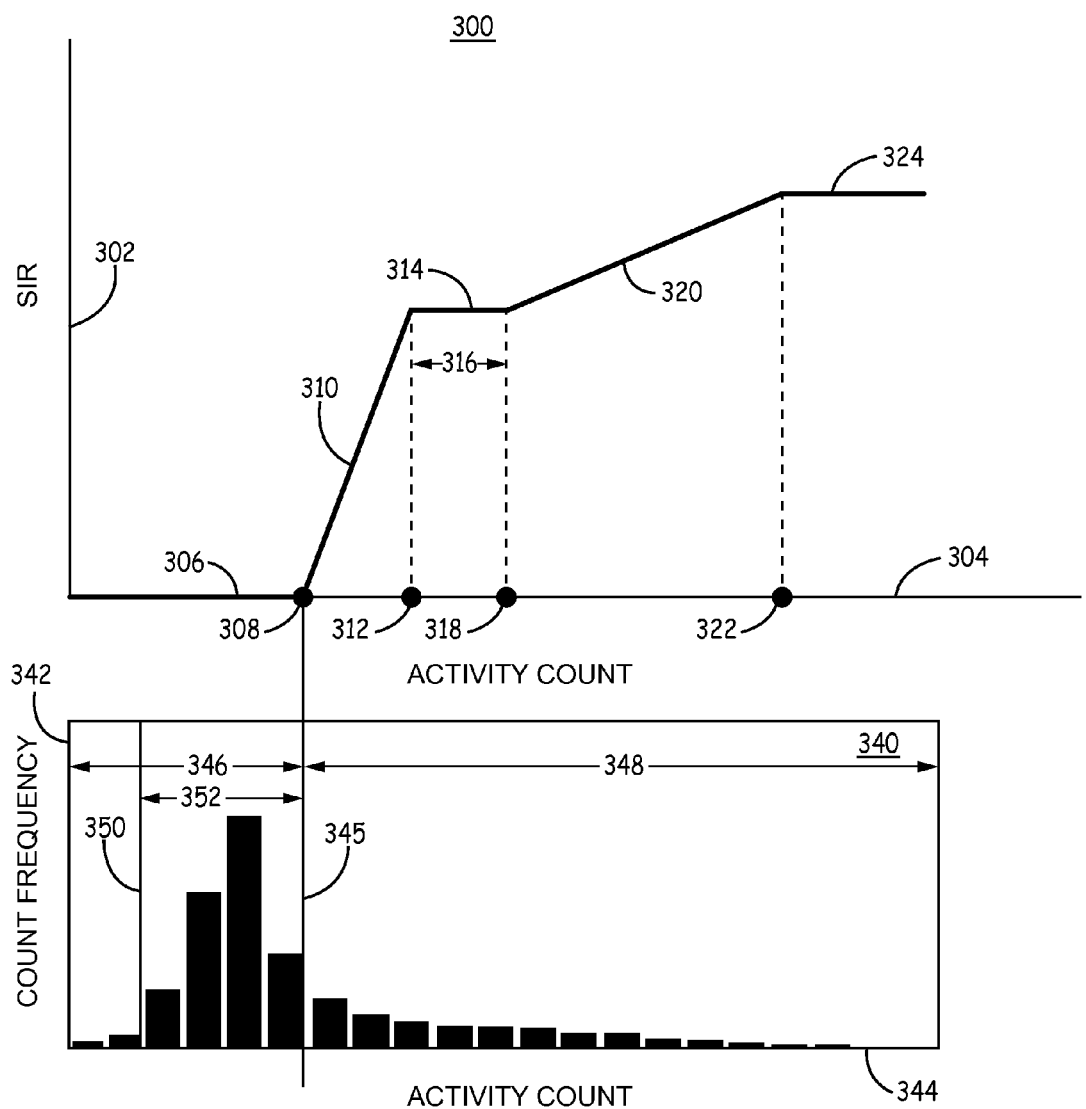
FIG. 4 is a plot of a sensor-indicated rate (SIR) transfer function that may be used by the pacemaker of FIG. 3 for controlling pacing pulse delivery according to one example.

FIG. 4 is a plot 300 of a sensor-indicated rate (SIR) transfer function that may be used by pacemaker 100 for controlling therapies delivered to heart 8 according to one example. Activity sensor 212 may be an accelerometer that produces a signal correlated to patient body motion. Activity metrics may be computed by pacemaker control module 206 from the activity sensor signal as a count of the total number of threshold crossings of the accelerometer signal or an integrated value of the accelerometer signal over a predetermined n-second interval, e.g., a 2-second interval, both of which are generally referred to herein as "activity counts." The SIR transfer function shown in FIG. 4 may be established using activity counts determined from the accelerometer signal that reflect a patient's activity profile over a typical day or week, user-programmed parameters or a combination of both.

In plot 300, SIR is plotted along the y-axis 302 as a function of activity count plotted along the x-axis 304. Pacemaker control module 206 may establish a lower rate (LR) set point 308 based on an analysis of the activity counts determined over an interval of time. When pacemaker 100 is enabled to provide rate-responsive pacing based on activity counts determined from the activity sensor signal, the pacing rate is not adjusted above a lower rate 306, sometimes referred to as the "base pacing rate," as long as the activity counts are at or below the LR set point 308.

As the activity count increases above the LR set point 308, the SIR may be determined according to the established transfer function between the SIR and the activity count. For example, an activity of daily living (ADL) lower set point 312 and ADL upper set point 318 may be established as the lower and upper boundaries of an activity count range that is expected to encompass the patient's activity level during normal daily activities and moderate activity, such as moving about the house, driving a car, light daily chores, etc. The SIR may be increased from the lower pacing rate 306 to the ADL rate 314 according to a slope 310 between the LR set point 308 and the ADL lower set point 312. The SIR remains at the ADL rate 314 during the ADL range 316 between the ADL lower set point 312 and the ADL upper set point 318. An activity count above the upper ADL set point 318 will cause the pacemaker 100 to adjust the SIR according to a second slope 320 as a function of activity count up to a maximum upper rate set point 322. The SIR is set to the maximum upper pacing rate 324 for all activity counts greater than the maximum upper rate set point 322. Each of the lower ADL set point 312, upper ADL set point 318 and maximum upper rate set point 322 may be tailored to a patient's particular needs based on the patient's activity count history.

The LR set point 308 and a loss of capture threshold 350 less than the LR set point 308 may be established by the pacemaker 100 based on an analysis of activity counts (or other activity metric) sampled over an adjustment interval in some examples. For instance, an activity count may be determined every two seconds over a 24-hour adjustment interval. The activity count value at a predetermined percentile 345 of all activity count values accumulated over the adjustment interval is selected as the LR set point 308 in one example. The predetermined percentile 345 may be established as the percentage of time the patient is expected to require pacing at the LR 306, which can also be thought of as the percentage of time that the patient is expected to be at rest or non-active. The activity counts in a resting range 346 extending from an activity count of 0 up to the previously established percentile 345 represent activity counts that may occur when the patient is at rest, e.g., sleeping, napping, sitting or otherwise inactive, and not requiring a pacing rate greater than the lower rate 306 to meet metabolic demand. The activity counts below percentile 345 are highly likely to be due primarily to heart motion and do not represent physical activity of the patient corresponding to an increase in metabolic demand.

The activity count values in a non-resting activity range 348 extending from the previously established percentile 345 to a maximum possible activity count represent activity counts that are expected to occur when the patient is active (not resting) and requires a pacing rate greater than the LR 306 to meet the patient's metabolic demand. To illustrate, the percentile 345 may be selected as 85% such that the SIR is at the LR 306 approximately 85% of the time and will be increased above the LR 306 approximately 15% of the time.

The analysis of the activity counts over an adjustment interval may be thought of in terms of a frequency plot 340. The number or frequency of activity counts occurring during a predefined time interval is shown along the y-axis 342 for each activity count value shown along the x-axis 344. In one example, the range of possible activity count values may be divided into predetermined activity count bins. The activity counts occurring in each bin are counted over the predefined time interval. The activity count bin at the predetermined patient activity percentile 345 is identified and set as the LR set point 308.

The LR set point 308 may be increased or decreased over time based on accumulated activity counts in order to maintain the number of activity counts that are greater than the LR set point 308 within a range of an expected number of activity counts greater than the LR set point. Continuing with the example given above, if the patient activity percentile 345 is 85%, the activity counts in range 348 greater than the LR set point 308 are expected to be approximately 15% of all the activity counts determined over a given time interval. If more than 15% of the activity counts are greater than the LR set point 308 during a predetermined time interval, the LR set point 308 may be increased. If less than 15% of the activity counts are greater than the LR set point 308, the LR set point 308 may be decreased by pacemaker control module 206. A pacemaker and methods for establishing a LR set point are generally disclosed in commonly-assigned U.S. patent application Ser. No. 14/552,758, filed on Nov. 25, 2014, hereby incorporated herein by reference in its entirety.

In addition to establishing LR set point 308, pacemaker control module 206 may establish a loss of capture (LOC) threshold 350 for detecting loss of pacing capture. The LOC threshold 350 is less than the LR set point 308 and may be defined as a percentile of all activity counts determined over a given time interval, e.g., the first percentile, second percentile or fifth percentile of all activity counts. Alternatively, the LOC detection threshold 350 may be defined as an activity count that is a percentage of the LR set point 308, e.g., 10% of the LR set point 308. For example, if the LR set point 308 is 15, the LOC threshold 350 may be set to an activity count of 2. A normal resting range 352 of activity count values occurring between the LR set point 308 and the established LOC detection threshold 350 represents the range of a vast majority, e.g., 90% or more, of the activity count values that are expected to occur when the patient is in a resting state when the activity count value is due primarily to normal heart motion. An activity count less than the normal resting range 352 indicates a significant decrease in heart motion, e.g., asystole, which is evidence for detecting LOC.

An activity count that is less than the LOC detection threshold 350, therefore, indicates that heart motion that normally contributes to the activity sensor signal has diminished significantly. For example, a pacemaker-dependent patient may be implanted with RA pacemaker 12 for providing atrial pacing when atrioventricular conduction is intact or implanted with RV pacemaker 14 for providing ventricular pacing if the patient presents atrioventricular conduction block. If LOC occurs in either heart chamber, heart motion contribution to the activity sensor signal may decrease significantly if asystole occurs. This significant reduction in heart motion detected based on a low activity count supports a LOC detection by control module 206. For example, if RV pacemaker 14 fails to capture in a patient with AV conduction block, the LOC may be detected based on a decrease in the activity count. If the RA pacemaker 12 fails to capture the right atrium in a patient with AV conduction intact, ventricular asystole may follow (when RV pacemaker 14 is not present). The RA pacemaker activity sensor signal may be diminished due to a lack of heart motion contribution leading to a LOC detection.

Figure 5:
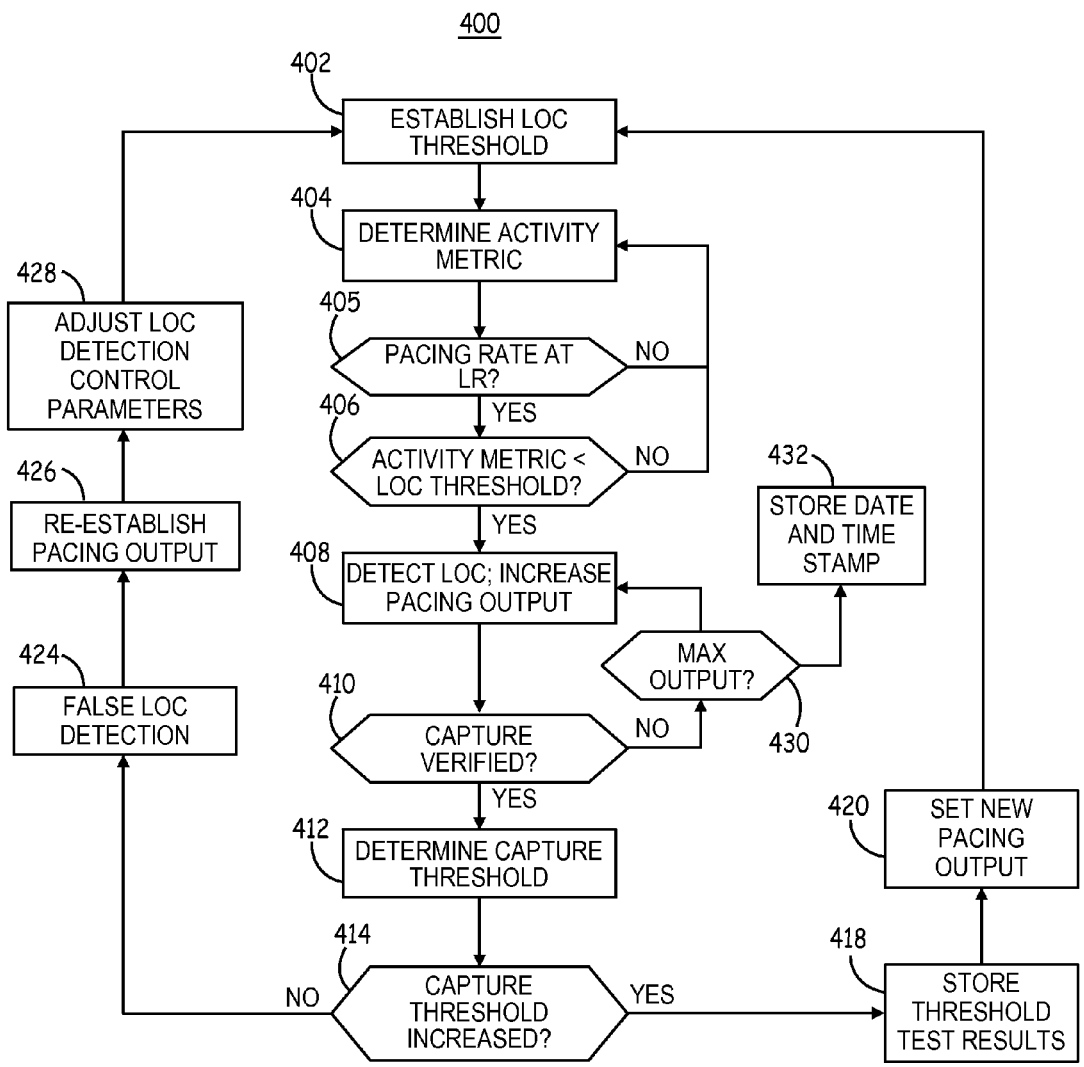
FIG. 5 is a flow chart of a method performed by the pacemaker of FIG. 3 for detecting loss of capture.

FIG. 5 is a flow chart 400 of a method performed by pacemaker 100 for detecting loss of capture. At block 402, a LOC threshold, also referred to herein as a "LOC detection threshold," is established. The LOC threshold may be programmed by a user or may be determined automatically by pacemaker 100. The LOC threshold may be automatically set to an activity metric value that is a predetermined percentile of all activity metrics determined over a given interval of time, e.g. one day, one week or other time period. For example, control module 206 may determine the first or second percentile activity count of all 2-second activity counts accumulated over a predetermined monitoring interval. Other examples of methods performed by control module 206 for establishing the LOC threshold are described below.

At block 404, control module 206 determines an activity metric, e.g., a 2-second activity count, from the activity sensor signal. Control module 206 may determine an activity metric at regular time intervals such as 2-second activity counts for use in determining a SIR. These 2-second activity counts may be used in on-going capture monitoring as well as rate responsive pacing control. For example whenever the SIR is at the lower rate and no tachyarrhythmia is being detected, every 2-second activity count may be compared to the LOC threshold.

In other examples, the activity metric may be used for verifying capture at scheduled times according to a capture management protocol. For example, the activity metric may be determined at block 404 whenever the pacing rate is at the lower rate (patient is inactive), nightly when the patient is at rest, or other scheduled basis. In this case, rate responsive pacing may be disabled but the activity metric normally used for controlling rate responsive pacing may be determined throughout a monitoring interval to establish the LOC threshold at block 402 then determined at scheduled times or continuously to monitor for LOC.

In some examples, the activity metrics that are being determined on an on-going basis are compared to the LOC threshold at block 406. If the activity metric is not less than the LOC threshold, the control module 206 determines the next activity metric. LOC is not detected. The process returns to block 404 to determine the next activity metric.

In other examples, the activity metric may not be compared to the LOC threshold at block 406 unless the pacing rate is at or near the lower rate (LR), e.g., within 10 beats per minute of the LR, as determined at block 405. If a SIR is greater than the LR based on an analysis of the activity metric, the activity metric is greater than the LR set point and therefore greater than the LOC threshold. No further comparison need be made. If the patient is active, the activity metric will be greater than the LOC threshold. If the activity metric is sustained at values greater than the LOC threshold, pacing at a SIR is supporting the sustained activity and therefore successful capture is likely. Other examples that enable activity metric-based LOC detection when the SIR is greater than the pacing LR are described below in conjunction with FIG. 8.

In a patient with complete atrioventricular (AV) block, LOC results in asystole which is detected based on the activity metric being less than the LOC threshold at block 406. In some examples, a single activity count less than the LOC threshold 350 shown in FIG. 4 results in a LOC detection. In other examples, LOC detection criteria applied at block 406 may require that two or more activity metrics be less than the LOC threshold, e.g., at least two consecutive activity counts, may be required. In a patient with incomplete AV block, some ventricular activity may occur despite LOC due to AV conduction on some beats resulting in a less diminished activity metric during LOC. As such, in some patients, the LOC detection criteria based on the activity sensor signal may be defined to include more than one activity metric being less than the LOC threshold and/or a less stringent LOC threshold. In other words, a higher LOC threshold 350 (shown in FIG. 4) may be used when the patient has some intrinsic AV conduction due to incomplete AV block than when a patient has complete AV block.

As such, more than one LOC threshold may be defined. A first LOC threshold used during continuous pacing may be established and a second LOC threshold, higher than the first LOC threshold, may be established for use during non-continuous pacing, e.g., when intrinsic events are being sensed intermittently during pacing, or for use when intrinsic events are sensed during an activity metric interval despite pacing. LOC detection criteria applied at block 406 may be selected by control module 206 based on whether or not R-waves have been sensed during a 2-second activity count interval (or other time interval over which the activity metric is determined).

If LOC detection criteria based on at least one activity metric being less than the LOC threshold are met at block 406, control module 206 detects LOC and controls pulse generator 202 to increase the pacing pulse output at block 408. The pacing pulse output may be increased by increasing the pacing pulse amplitude and/or pacing pulse width.

At block 410, control module 206 verifies that capture has occurred after increasing the pacing pulse output. Capture may be verified by detecting an electrical evoked response. The electrical evoked response may be detected by analyzing the EGM signal received from sensing module 204. The electrical evoked response may be detected by control module 206 by setting an evoked response detection window following the pacing pulse and determining if an evoked R-wave is present during the detection window based on an amplitude threshold crossing, maximum peak amplitude, waveform morphology or other evoked response detection criteria. Evoked response detection is generally described in U.S. Pat. No. 7,123,963 (Sawchuk, et al.), incorporated herein by reference in its entirety.

If an electrical evoked response is not detected at block 410, the pacing output may be increased again by returning to block 408 until capture is verified. It is recognized that is some examples, capture is verified based on detecting evoked responses following more than one pacing pulse. For example, at least two consecutive evoked responses may be required to be detected in order to verify that the increased pacing output has successfully captured the paced heart chamber. In another example, evoked response detection following two out of three pacing pulses may be required to verify capture. Additionally or alternatively, capture may be verified at block 410 based on an activity metric value exceeding the LOC threshold after increasing the pacing output or based on other sensor signals, such as a pressure signal.

It is recognized that in some cases, a pacing output may reach a maximum value and capture cannot be verified. If capture is not verified at block 410, and a maximum output is reached as determined at block 430, a date and time stamp may be stored at block 432 marking this capture failure event. The capture failure event may be caused by the death of the patient, in which case the date and time stamp may mark the approximate time of death.

After verifying capture subsequent to the increased pacing pulse output, a capture threshold search may be performed by control module 206 to determine the pacing capture threshold at block 412. A capture threshold search may be performed by controlling pulse generator 202 to iteratively reduce the pacing pulse output (e.g., decrease the pulse amplitude or the pulse width) until capture is lost, e.g., based on a disappearance of the electrical evoked response following the pacing pulse(s).

The capture threshold is compared to a previously determined capture threshold at block 414. If the capture threshold has increased compared to a most recent previously-determined capture threshold, the new capture threshold is stored in memory 210 at block 418 for use in setting pacing output by control module 206 and for comparing to future capture thresholds.

At block 420, control module 206 sets the pacing output of pulse generator 202 based on the new capture threshold, e.g., to a pulse amplitude and/or pulse width that is at least or greater than the capture threshold. Typically, the pacing output is set at a safety margin greater than the capture threshold. The safety margin may be relatively small, e.g., 0.5 Volts or less, in order to conserve battery longevity of pacemaker 100. Monitoring the activity metric for evidence of LOC may enable a small safety margin to be used by pacemaker 100 with adjustments to pacing output made as needed to maintain capture.

If the capture threshold has not increased compared to the previously determined capture threshold, as determined at block 414, the activity metric-based LOC detection is deemed false at block 424. At block 426, the previous pacing output is re-established to continue pacing based on the determined capture threshold.

At block 428, the control module 206 may adjust LOC detection control parameters to reduce the likelihood of another false LOC detection. For example, the LOC threshold may be decreased. Control module 206 may decrease the LOC threshold temporarily for a predetermined interval of time, e.g., one hour or more. Decreasing the LOC threshold may avoid frequent capture threshold searches caused by false LOC detection based on the activity metric. Alternatively, LOC detection based on the activity sensor signal may be disabled for a predetermined interval of time, e.g., for one hour.

The LOC threshold may be updated at block 402 as more activity metrics are accumulated. For example, every 24 hours or other predetermined update interval, the LOC threshold may be re-established based on the activity metrics accumulated over the preceding update interval. In other examples, if the LR set point or any other set point used for defining the SIR transfer function as shown in FIG. 4 is adjusted, the LOC threshold may be adjusted.

Figure 6:
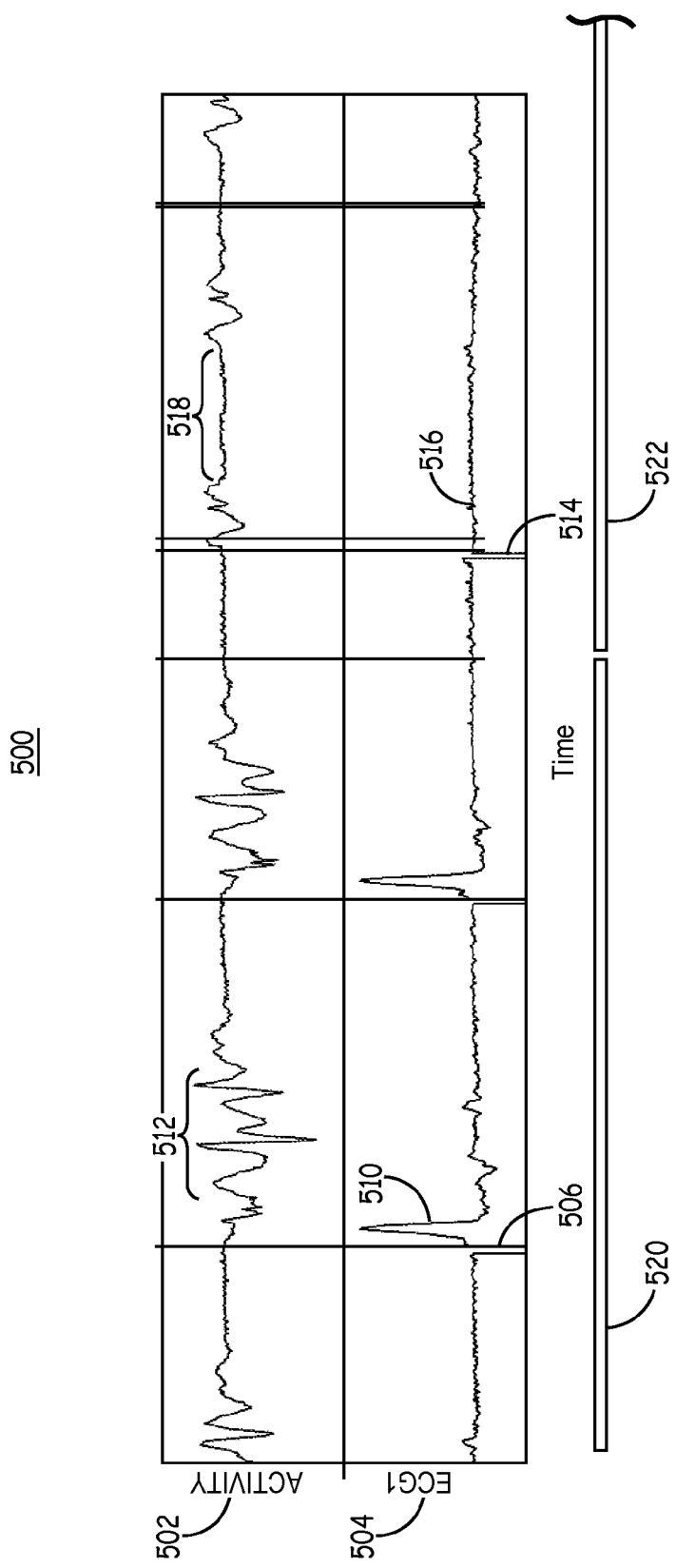
FIG. 6 is a plot of an activity sensor signal and a cardiac electrical signal.

FIG. 6 is a plot 500 of an activity sensor signal 502 and a cardiac electrical signal 504. When a pacing pulse 506 is delivered that meets or exceeds the capture threshold, an electrical evoked response 510 follows the pacing pulse 506. The electrical evoked response 510 may be detected by control module 206 based on amplitude, waveform morphology analysis, or other signal analysis criteria as described above for verifying capture after the pacing output has been increased due to LOC detection based on the activity sensor signal and/or during a capture threshold search.

The activity sensor signal 502 is shown as a raw accelerometer signal in this example. The mechanical evoked response 512 is observed on activity sensor signal 502 following the electrical evoked response 510. The activity sensor signal 502 may be rectified and summed over an activity count interval 520 or rectified activity sensor signal crossings of an activity threshold may be counted during the activity count interval 520. The activity count interval 520 is shown as a 2-second interval that is restarted every 2 seconds to obtain activity counts every two seconds on an on-going basis. As such, the activity count interval 520 is not a window set in response to a pacing pulse 506 or in any timed relation to the cardiac cycle. During the 2-second activity count interval 520, the mechanical evoked response 512 will contribute to the total activity count to produce activity counts in the normal resting range 352 (FIG. 5) when the patient is inactive.

A pacing pulse 514 that does not meet the capture threshold does not produce an electrical evoked response as observed by the baseline signal 516 of cardiac electrical signal 504 following pacing pulse 514. Control module 206 may confirm electrical loss of capture based on the absence of an electrical evoked response following a pacing pulse when LOC is detected based on the activity sensor signal 502.

In FIG. 6, mechanical loss of capture is observed as the baseline portion 518 of the activity sensor signal 502 following the pacing pulse 514 at the approximate time that a mechanical evoked response is expected to be observed. In this example, some deflection of the activity sensor signal 502 is observed following pacing pulse 514 due to atrial motion. The absence of the expected mechanical evoked response corresponding to ventricular systole following pacing pulse 514 will result in a decreased activity count obtained over activity count interval 522. If the activity count obtained over activity count interval 522 is less than the LOC threshold 350 (FIG. 4), LOC is detected by control module 206 based on the activity count. The LOC threshold 350 may be established manually by a clinician or by performing a capture threshold search as described below.

Figure 7:
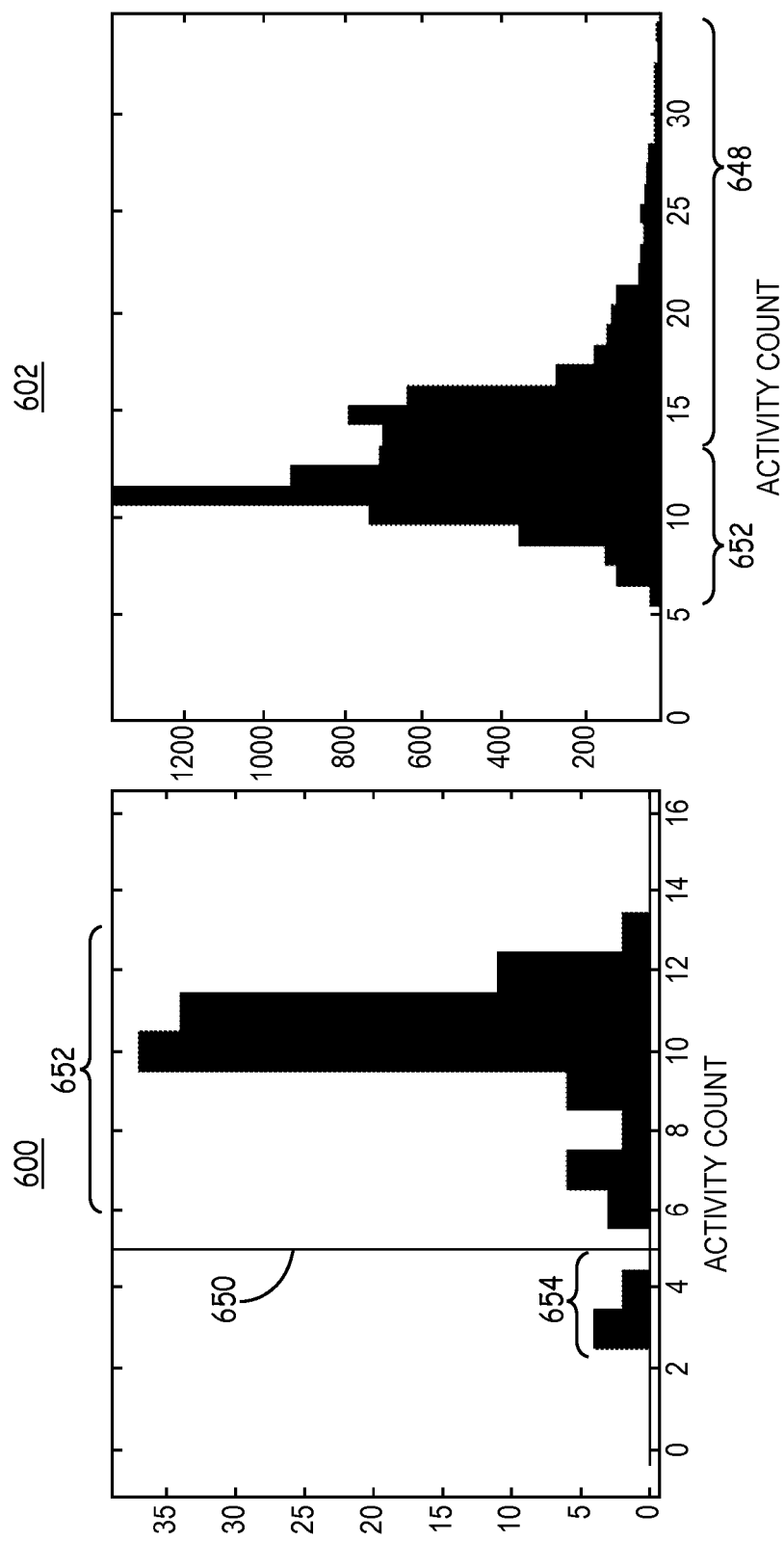
FIG. 7A is a bar graph of activity counts during five capture threshold searches that include loss of capture (LOC) at sub-threshold pacing.
FIG. 7B is a bar graph of activity counts during a 24-hour period that does not include incidents of LOC.

FIG. 7A is a bar graph 600 of activity counts during five capture threshold searches that include LOC at sub-threshold pacing. FIG. 7B is a bar graph 602 of activity counts during a 24-hour period that does not include incidents of LOC. In this illustrative example, the activity count ranges from 3 to 13 during the sequence of five capture threshold searches and no physical activity (FIG. 7A). During the 24-hour period of normal activity and no LOC, activity counts range from 6 to over 30 (FIG. 7B). Accordingly, a normal resting range 652 may include the range of activity counts from 6 to 13 shown in FIG. 7A, which includes normal heart motion associated with successful pacing capture. Activity counts greater than the normal resting range 652 represent the non-resting activity count range 648.

A LOC threshold 650 may be set at 5 in this example since no activity counts less than 5 are observed in FIG. 7B, when no LOC occurs over the 24 hour period. Activity counts 654 less than 5 shown in FIG. 7A represent the LOC that occurs during the capture threshold searches when the pacing pulse output is decreased below the capture threshold.

The bar graphs 7A and 7B illustrate methods for automatically establishing the LOC threshold 650 by control module 206 at block 402 of FIG. 5. In one example, the LOC threshold 650 may be established by the control module 206 based on activity counts obtained during one or more capture threshold searches. The control module 206 may control pulse generator 202 to decrease the pacing pulse output until an electrical evoked response is no longer detected as seen in FIG. 6. The activity counts obtained over activity count intervals that include loss of electrical evoked response may be determined, such as activity count interval 522 shown in FIG. 6. The LOC threshold 650 may be defined so that it separates activity counts 652 obtained during activity count intervals 520 (FIG. 6) in which pacing resulted in capture from the activity counts 654 obtained over activity count intervals 522 (FIG. 6) that include pacing pulses delivered below the capture threshold.

In another example, electrical evoked response monitoring may be performed over a 1-, 2-, 8-, or 24-hour period or other time interval to obtain activity counts known to correspond to successful capture, e.g., as shown by FIG. 7B. The LOC threshold 650 may be set below activity counts known to include heart motion during successful capture. The LOC threshold may be set at 5 in the example of FIG. 7B since no activity counts below 5 occurred during this period of normal activity and no LOC.

In yet another example, one or more sub-threshold pacing pulses may be delivered intentionally during an activity count interval to obtain an activity count during known LOC and one or more supra-threshold pacing pulses may be delivered during a next activity count interval to obtain an activity count during known capture. A LOC threshold 650 may be established that separates the known LOC activity count from the known capture activity count. Such a test performed to establish a LOC threshold 650 may be performed when the patient is known to be at rest, e.g. at night, or under the supervision of a clinician.

Figure 8:
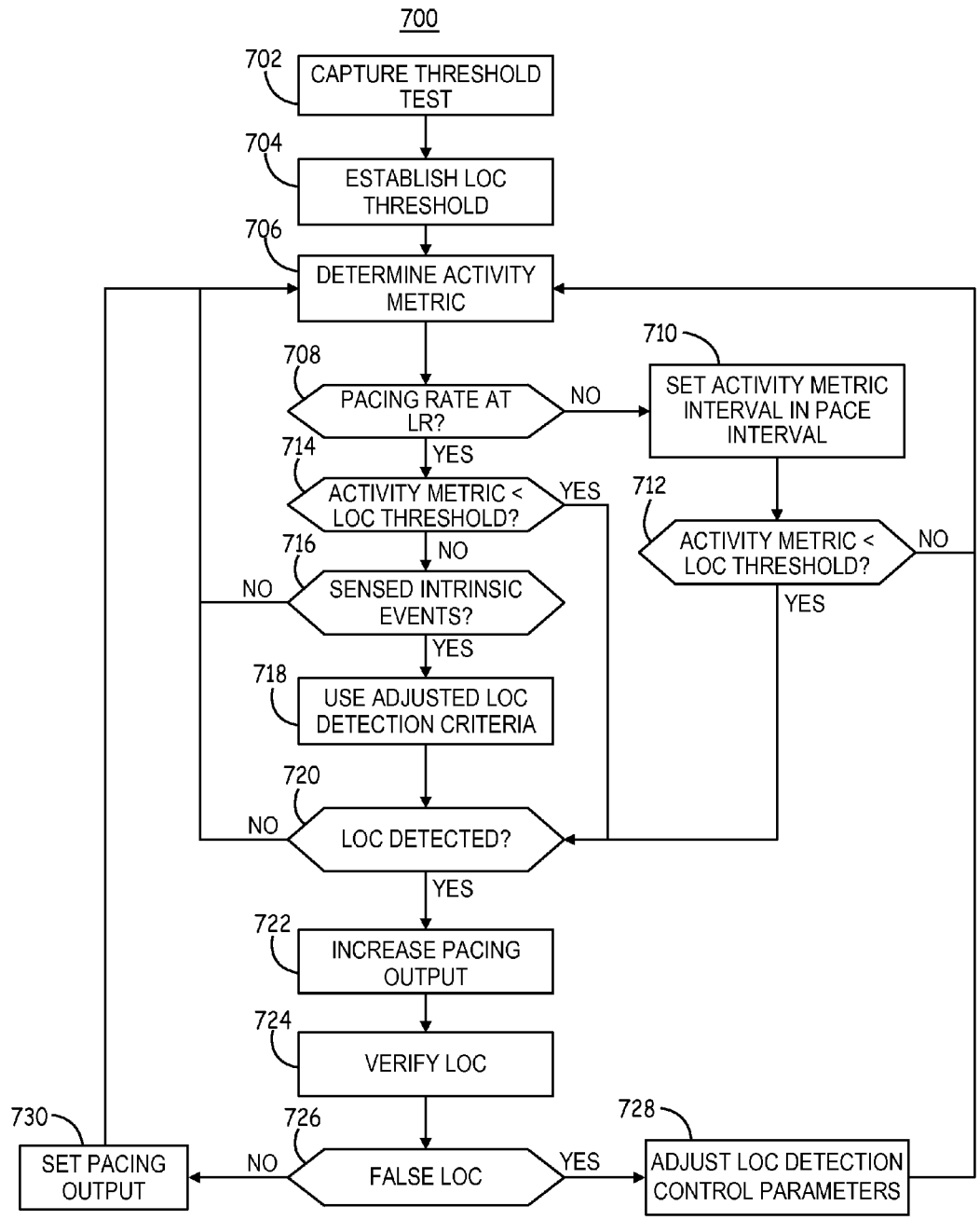
FIG. 8 is a flow chart of a method for detecting LOC according to another example.

FIG. 8 is a flow chart 700 of a method for detecting LOC according to another example. At block 702, control module 206 may execute a capture threshold test to set the pacing output at a safety margin above the capture threshold. A capture threshold test may be performed at regular scheduled intervals, e.g., once every 24 hours, using electrical evoked response detection for verifying capture.

At block 704, the LOC threshold based on an activity metric is established. As described above, the LOC threshold may be based on activity metrics determined over a preceding time interval. In some examples, the LOC threshold is set to the first or second percentile of all activity metrics determined over at least a 24-hour period. In another example, the LOC threshold may be established based on an activity metric determined during the capture threshold test performed at block 702. The LOC threshold may be set below activity metrics obtained over activity metric intervals that included electrical evoked responses (supra-threshold pacing) and above any activity metrics determined over activity metric intervals that included sub-threshold pacing pulses resulting in electrical LOC.

At block 706, an activity metric is determined. The activity metric may be determined over an activity metric interval that is used for determining SIR, such as the 2-second activity counts described above. If the current pacing rate is greater than the lower rate (LR), due to a SIR greater than the LR, as determined at block 708, an adjusted activity count interval may be set at block 710. When the SIR is greater than the LR due to patient activity, the physical patient activity may mask a decreased contribution of heart motion to the activity sensor signal. As such, an adjusted activity count interval may be used to capture the activity sensor signal during a time interval following a pacing pulse that will include the mechanical evoked response if present.

With reference to FIG. 6, an adjusted activity count interval may be started beginning at pacing pulse 506, or after a short delay, e.g., 20 ms after pacing pulse 506. The adjusted activity count interval may extend for approximately 500 ms or less after the pacing pulse 506, depending on the pacing rate. For example, the adjusted activity count interval may correspond to less than 50% of the pacing interval that is set according to the SIR to include the expected mechanical evoked response 512.

An activity metric determined over the adjusted activity metric interval is compared to a LOC threshold at block 712. The activity metric may be a threshold crossing count or summation of the activity sensor signal sample points determined over the adjusted activity metric interval in the same manner that the activity metric is determined over the non-adjusted activity metric interval at block 706. Physical patient activity may still contribute to the activity metric determined for the adjusted activity metric interval, however, greater sensitivity to a diminished contribution by heart motion to the activity sensor signal due to LOC is achieved by narrowing the activity metric interval to an interval that is approximately limited to an expected time of the mechanical evoked response.

The activity metric determined over the adjusted interval is compared to a LOC threshold at block 712, which may be the same LOC threshold used for comparisons to activity metrics determined over non-adjusted activity metric intervals or an adjusted LOC threshold. The LOC threshold may be adjusted to a lower LOC threshold since the activity metric is being determined over a relatively shorter time interval.

On the other hand, a lower LOC threshold may be too insensitive to detect LOC during physical activity due to the physical activity contribution to the activity sensor signal. The control module 206 may therefore be configured to "learn" an appropriate LOC threshold for use with an adjusted activity metric interval over time. If the activity metric is less than the LOC threshold at block 712, LOC detection is made at block 720. The pacing output may be increased at block 722, and the detected LOC may be verified at block 724 by performing a capture threshold search using electrical evoked response detection at block 724 to verify the capture threshold has increased compared to a previous capture threshold. If the detected LOC is determined to be a false detection of LOC based on no change in the capture threshold, as described previously in conjunction with FIG. 5, the LOC detection criteria may be adjusted at block 728. The adjusted activity metric interval may be adjusted to a different interval and/or the LOC threshold applied to an activity metric determined over the adjusted interval may be adjusted. In this way, the activity metric interval and LOC threshold used during patient activity and pacing above the LR may be adjusted to values that provide greater specificity of LOC detection during activity.

In some examples, the adjusted activity metric interval set at block 710 may be a segmented interval that includes multiple segments corresponding to the mechanical evoked response 512 for each of two or more pacing pulses. In this way, the total duration of the activity metric interval may be kept the same, e.g., 2 seconds, but the total duration of the activity metric interval is segmented over multiple pacing cycles to primarily capture the interval of the expected mechanical evoked response. A threshold crossing count or a summation of rectified activity sensor signal sample points may be continued from a previous segment of the segmented activity metric interval until a predetermined total duration of the activity metric interval is reached. For example, the activity metric used for LOC detection during activity may be determined as the combined activity counts determined over four 500 ms intervals set in timed relation to pacing pulses to encompass the expected mechanical evoked response.

The LOC threshold established at block 704 may be relevant for comparison to an activity metric determined over the segmented activity metric interval since the total time duration of the activity metric interval is the same. Alternatively, an increased LOC threshold may be used to account for the contribution of physical activity to the activity sensor signal when pacing at a SIR greater than the LR. When an adjusted activity metric interval is used at block 710 for LOC detection, it is recognized that the standard activity metric interval may continue to be used simultaneously for determining activity metrics for monitoring patient activity and determining SIR for controlling pacing rate.

If the current pacing rate is at the LR at block 708 and rate responsive pacing is enabled, the patient is inactive or at rest; the SIR is at the LR. In this case, the activity metric is compared to the established LOC detection threshold at block 714. If the activity metric is less than the LOC detection threshold, LOC is detected at block 720. The LOC response may be provided as described previously by increasing pacing output at block 722 and verifying the LOC detection as being valid by performing a capture threshold test with electrical evoked response sensing at block 724. If the LOC detection is false as determined at block 726, the LOC threshold or other LOC detection control parameters may be adjusted at block 728. For example, activity metric-based LOC detection may be disabled for a predetermined interval of time and/or the LOC threshold may be decreased.

If the activity metric is not less than the LOC threshold at block 714, the control module 206 may determine if one or more intrinsic cardiac events, e.g. a P-wave in the atrium or an R-wave in the ventricle, are sensed by the sensing module 204 during the activity metric interval. If control module 206 received a sense event signal from sensing module 204 (e.g., an R-sense signal in RV pacemaker 14 or a P-sense signal in RA pacemaker 12), adjusted LOC detection criteria may be applied at block 718. An increased LOC threshold and/or an increased number of activity metrics may compared to the LOC threshold in order to detect LOC. For example, at least two consecutive activity metrics may be required to reach an increased LOC threshold in order to detect LOC during pacing pulse delivery at the LR in the presence of sensed intrinsic events.

If LOC is not detected at block 720, the next activity metric is determined at block 706 and the process continues. If LOC is detected at block 720 based on the established or adjusted LOC threshold and/or a standard or adjusted activity metric interval, and verified at block 724 based on a capture threshold search, the pacing output may be adjusted at block 730 according to the new capture threshold determined at block 724. If the LOC detection is false as determined at block 726, LOC detection control parameters may be adjusted at block 728 as described previously.

The process shown by flow chart 700 may be restarted at block 702 whenever a capture threshold search is scheduled or performed for any reason. A new LOC threshold may be established at block 704 each time a scheduled capture threshold search is performed, e.g. every 24 hours or other predetermined time interval, and may be based on activity metrics measured during the capture threshold search and/or activity metrics accumulated since the last LOC threshold was established.

Thus, various embodiments of a medical device and method have been described for detecting pacing LOC based on an activity sensor signal. However, one of ordinary skill in the art will appreciate that various modifications may be made to the described embodiments without departing from the scope of the following claims.

The invention claimed is:

1. An implantable medical device, comprising:
   an activity sensor configured to generate a signal indicative of motion of a heart of a patient and physical activity of the patient;
   a pulse generator configured to generate and deliver pacing pulses to the patient's heart via a pair of electrodes coupled to the implantable medical device; and
   a control module coupled to the pulse generator and the activity sensor, the control module being configured to:
   compute an activity metric from the activity sensor signal over an activity metric interval;
   compare the activity metric to a loss of capture detection threshold;
   detect loss of capture by the delivered pacing pulses in response to the activity metric being less than the loss of capture detection threshold; and
   increase a pacing pulse output in response to detecting the loss of capture; and
   wherein the control module is further configured to:
   determine a sensor indicated pacing rate based on the activity metric; and
   set a pacing pulse rate responsive to the sensor indicated pacing rate.

2. The device of claim 1, wherein the control module is further configured to:
   adjust at least one of the loss of capture detection threshold and the activity metric interval responsive to the pacing rate being set at a sensor indicated pacing rate that is greater than a predetermined base rate.

3. The device of claim 1, wherein the control module is further configured to:
   accumulate a plurality of activity metric values; and
   establish the loss of capture detection threshold based on at least a portion of the plurality of activity metric values.

4. The device of claim 3, further comprising a sensing module for sensing a cardiac electrical signal, wherein the control module is further configured to:
   accumulate the plurality of activity metric values by:
      performing a capture threshold search to determine a capture threshold indicated by the sensed cardiac electrical signal; and
      accumulating the plurality of activity metric values during the capture threshold search, wherein the loss of capture detection threshold is established based on the at least one of the plurality of activity metric values accumulated during the capture threshold search.

5. The device of claim 1, wherein the control module is further configured to:
   perform a capture threshold search to determine a capture threshold in response to detecting the loss of capture;
   compare the determined capture threshold to a previously determined capture threshold; and
   adjust a loss of capture detection control parameter in response to the determined capture threshold being equal to or less than the previously determined capture threshold.

6. The device of claim 5, wherein the control module is configured to adjust the loss of capture detection control parameter by decreasing the loss of capture threshold.

7. An implantable medical device, comprising:
   an activity sensor configured to generate a signal indicative of motion of a heart of a patient and physical activity of the patient;
   a pulse generator configured to generate and deliver pacing pulses to the patient's heart via a pair of electrodes coupled to the implantable medical device; and
   a control module coupled to the pulse generator and the activity sensor, the control module being configured to:
   compute an activity metric from the activity sensor signal over an activity metric interval;
   compare the activity metric to a loss of capture detection threshold;
   detect loss of capture by the delivered pacing pulses in response to the activity metric being less than the loss of capture detection threshold; and
   increase a pacing pulse output in response to detecting the loss of capture; and
   wherein the control module is configured to determine the activity metric by one of:
   rectifying the activity sensor signal and counting a number of activity threshold crossings of the activity sensor signal during the activity metric interval, and
   rectifying the activity sensor signal and summing all sample point amplitudes of the rectified activity sensor signal during the activity metric interval.

8. An implantable medical device, comprising:
   an activity sensor configured to generate a signal indicative of motion of a heart of a patient and physical activity of the patient;
   a pulse generator configured to generate and deliver pacing pulses to the patient's heart via a pair of electrodes coupled to the implantable medical device; and
   a control module coupled to the pulse generator and the activity sensor, the control module being configured to:
   compute an activity metric from the activity sensor signal over an activity metric interval;
   compare the activity metric to a loss of capture detection threshold;
   detect loss of capture by the delivered pacing pulses in response to the activity metric being less than the loss of capture detection threshold; and increase a pacing pulse output in response to detecting the loss of capture; and further comprising a sensing module configured to receive a cardiac electrical signal from the heart developed across a sensing electrode pair coupled to the implantable medical device, sense an intrinsic cardiac event from the cardiac electrical signal, and pass a cardiac sense event signal to the control module in response to sensing the intrinsic cardiac event, wherein the control module is further configured to:

receive cardiac sense event signals from the sensing module, responsive to the activity metric being greater than the loss of capture threshold, determine if an intrinsic sensed event occurs during the activity metric interval based on the received cardiac sense event signals; and responsive to occurrence of the intrinsic sensed event during the activity metric interval, adjusting a loss of capture detection control parameter.

9. The device of claim 8, wherein the control module is configured to adjust the loss of capture detection control parameter by at least one of increasing the loss of capture detection threshold and increasing a number of activity metrics less than the loss of capture detection threshold that are required to detect the loss of capture.

10. An implantable medical device, comprising:

an activity sensor configured to generate a signal indicative of motion of a heart of a patient and physical activity of the patient;

a pulse generator configured to generate and deliver pacing pulses to the patient's heart via a pair of electrodes coupled to the implantable medical device; and a control module coupled to the pulse generator and the activity sensor, the control module being configured to:

compute an activity metric from the activity sensor signal over an activity metric interval;

compare the activity metric to a loss of capture detection threshold;

detect loss of capture by the delivered pacing pulses in response to the activity metric being less than the loss of capture detection threshold; and increase a pacing pulse output in response to detecting the loss of capture; and further comprising a memory, wherein the control module is further configured to:

detect an occurrence of capture subsequent to increasing the pacing pulse output;

if capture is not detected, adjust the pacing pulse output incrementally up to a maximum pacing pulse output until capture is verified; and record a date and time stamp in the memory in response to the maximum pacing pulse output being reached without the detection of capture.

\* \* \* \* \*